(12) United States Patent
Lin et al.

(10) Patent No.: US 6,835,933 B2
(45) Date of Patent: Dec. 28, 2004

(54) SPECTRUM MEASURING APPARATUS

(75) Inventors: Yaomin Lin, Hsinchu (TW); Hau-Wei Wang, Taipei (TW); Ying-Cheun Spring Yeh, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 113 days.

(21) Appl. No.: 10/299,848

(22) Filed: Nov. 20, 2002

(65) Prior Publication Data

US 2003/0094573 A1 May 22, 2003

(30) Foreign Application Priority Data

Nov. 21, 2001 (TW) ........................................ 90128816 A

(51) Int. Cl.⁷ ........................ G01N 21/35; G01N 21/64; G01N 21/65
(52) U.S. Cl. .............................. 250/339.05; 250/458.1; 356/301
(58) Field of Search ......................... 250/339.05, 458.1; 356/301

(56) References Cited

U.S. PATENT DOCUMENTS

| | | | | |
|---|---|---|---|---|
| 5,377,004 A | * | 12/1994 | Owen et al. | ................. 356/301 |
| 5,841,139 A | * | 11/1998 | Sostek et al. | .......... 250/339.12 |
| 6,070,093 A | * | 5/2000 | Oosta et al. | ................. 600/316 |
| 6,687,051 B1 | * | 2/2004 | Wang et al. | ................. 359/361 |

* cited by examiner

*Primary Examiner*—Constantine Hannaher
(74) *Attorney, Agent, or Firm*—Birch, Stewart, Kolasch & Birch, LLP

(57) ABSTRACT

A spectrum measuring apparatus for measuring infrared, Raman and fluorescence spectra. The spectrum measuring apparatus includes an infrared source, a laser source, an infrared up-conversion object lens, an object lens, a dual color lens, an ocular, a narrow band filter, a visible light image capturing device and a sample pedestal. The infrared spectrum is measured by the infrared up-conversion object lens. The Raman and fluorescence spectra are measured by the object lens.

11 Claims, 3 Drawing Sheets

SPECTRUM MEASURING APPARATUS

This nonprovisional application claims priority under 35 U.S.C. §119(a) on Patent Application No. 90128816 filed in TAIWAN on Nov. 21, 2001, which is herein incorporated by reference.

BACKGROUND OF THE INVENTION

1. Field of the Invention

The present invention relates to a spectrum measuring apparatus, and in particular to a spectrum measuring apparatus for measuring infrared, Raman and fluorescence spectra.

2. Description of the Related Art

A chemical component can be analyzed by infrared, Raman and fluorescence spectra, used in quantitative and qualitative analyses of organic and inorganic substances. The infrared and Raman spectra are vibration spectra that can analyze the functional group or the chemical bonding of a chemical component. The fluorescence spectrum is an electron jumping spectrum that analyzes the electronic structure of a chemical molecule. Nevertheless, there is no measuring device capable of measuring infrared, Raman and fluorescence spectra simultaneously.

SUMMARY OF THE INVENTION

An object of the invention is to provide a spectrum measuring apparatus for measuring infrared, Raman and fluorescence spectra. The spectrum measuring apparatus comprises a sample pedestal, an infrared source, a laser source, an infrared up-conversion object lens, an object lens, an ocular and a visible light image capturing device. A sample is placed on the sample pedestal. The infrared source outputs infrared light to the sample to generate infrared light having a vibration spectrum at which time the spectrum measuring apparatus measures the infrared spectrum. The laser source outputs single band laser to the sample at which time the spectrum measuring apparatus measures the Raman or fluorescence spectra. The infrared up-conversion object lens has an optical crystal and an infrared object lens. A dichroic film is formed on one side of the optical crystal. The infrared object lens receives the infrared light having the vibration spectrum and outputs collimated infrared light having the vibration spectrum to the optical crystal when the single band laser enters the optical crystal and is reflected by the dichroic film. The single band laser and the collimated infrared light having the vibration spectrum are coupled to sum-frequency light in the optical crystal. The single band laser is output to the sample via the object lens when the spectrum measuring apparatus measures the Raman or fluorescence spectra. The sample generates Raman light having the Raman spectrum or fluorescence having the fluorescence spectrum to pass through the object lens. The ocular images the sum-frequency light, the Raman light and the fluorescence to a predetermined position. The visible light image capturing device is disposed in the predetermined position to receive the sum-frequency light, the Raman light and the fluorescence.

Preferably, the spectrum measuring apparatus further comprises a dual color lens.

Preferably, the spectrum measuring apparatus further comprises a narrow band filter for preventing the single band laser from interfering with the visible light image capturing device.

Preferably, the spectrum measuring apparatus further comprises a concave lens and a convex lens.

Preferably, the spectrum measuring apparatus further comprises an infrared condenser set reflecting the infrared light from the infrared source to the sample.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
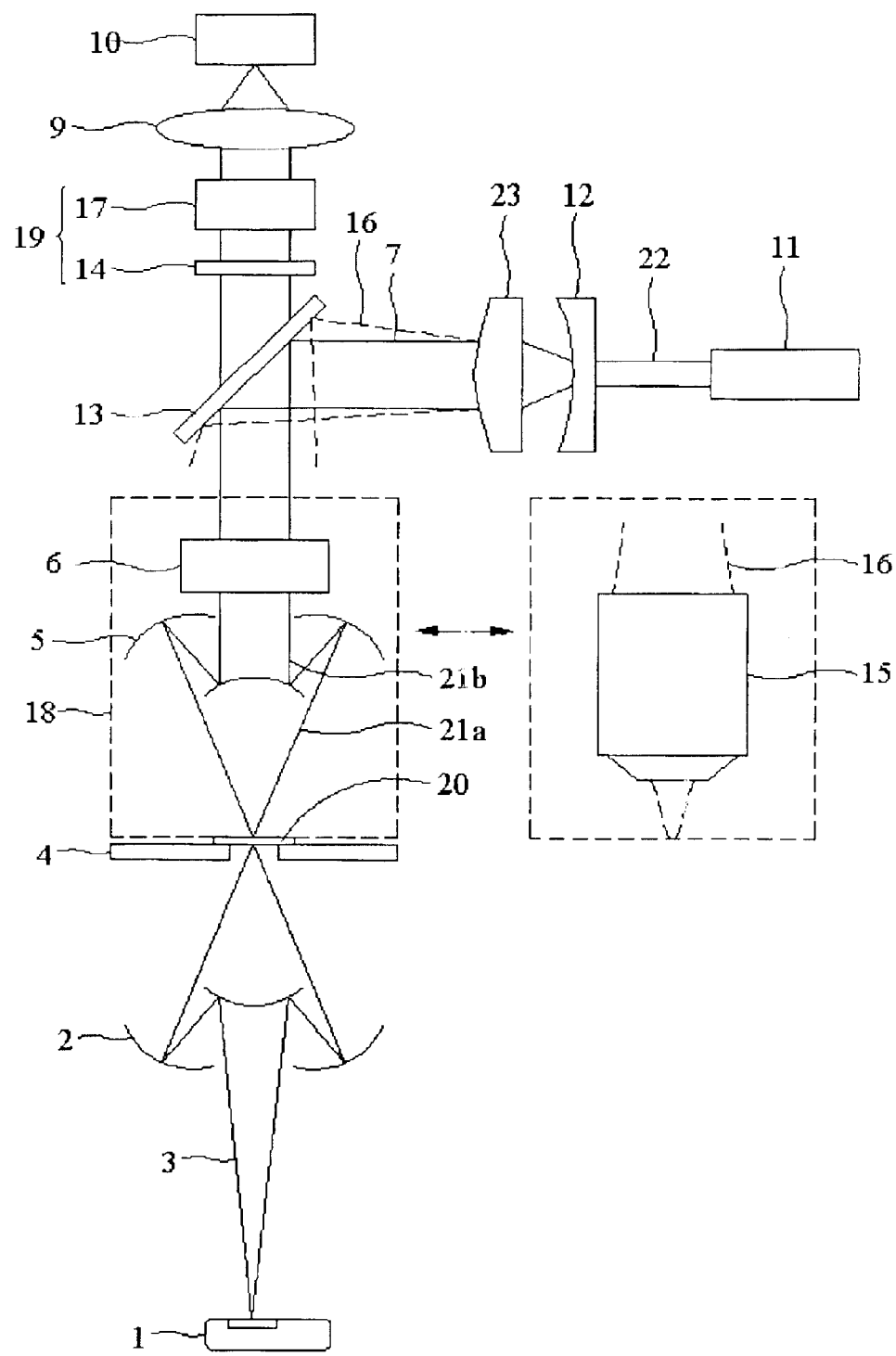
FIG. 1 is a schematic view showing the spectrum measuring apparatus of the invention for measuring infrared, Raman and fluorescence spectra.

Referring to FIG. 1, the present spectrum measuring apparatus comprises an infrared source 1, a laser source 11, an infrared up-conversion object lens 18, an object lens 15, a dual color lens 13, an ocular 9, a narrow band filter 19, a visible light image capturing device 10 and a sample pedestal 4. The infrared up-conversion object lens 18 further comprises an optical crystal 6 and three infrared object lenses 5. The Raman and fluorescence spectra are measured by the object lens 15. The infrared spectrum is measured by the infrared up-conversion object lens 18. Additionally, the spectrum measuring apparatus further comprises an infrared condenser set 2 for condensing infrared light 3 to a sample 20 when the infrared spectrum is measured.

As shown in FIG. 1, when the infrared spectrum is measured, the sample 20 is placed on the sample pedestal 4 and the infrared source 1 outputs infrared light 3. The infrared light 3 is condensed to the sample 20 by the infrared condenser set 2. The infrared light 3 reacts with the molecular functional group or the chemical bonding of the sample 20. Then, infrared light 21a having a vibration spectrum is generated. The infrared light 21a enters the infrared up-conversion object lens 18 having the optical crystal 6 and the infrared object lenses 5. The infrared object lens 5 is an IR infinity-corrected reflective object lens. Thus, the infrared light 21a having the vibration spectrum is reflected to infinity by the infrared object lenses 5. Namely, the infrared light 21a is reflected into collimated infrared light 21b by the IR infinity-corrected reflective object lenses 5.

As shown in FIG. 1, a visible light source 11, such as a laser, outputs single band visible light 22. The single band visible light 22 passes through a concave lens 12 and a convex lens 23 to become collimated single band visible light 7. The collimated single band visible light 7 is reflected to the infrared up-conversion object lens 18 by the dual color lens 13. Then, the collimated single band visible light 7 enters the optical crystal 6, such as a birefringence crystal or a quasi-phase matching crystal. Also, the collimated infrared light 21b enters the optical crystal 6.

Figure 2:
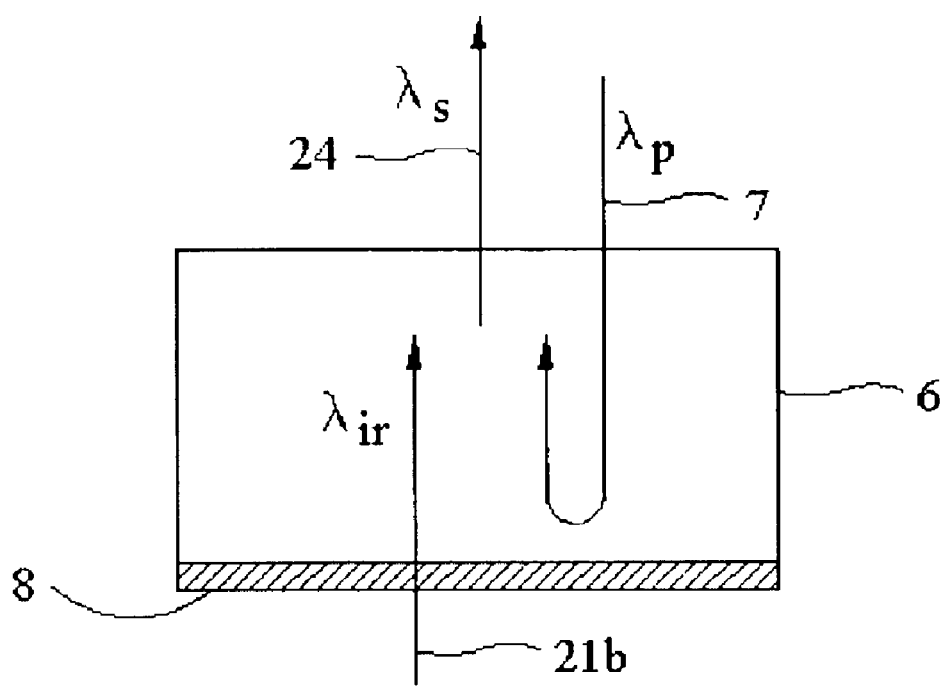
FIG. 2 is a schematic view showing a dichroic film formed on one side of the optical crystal.

Referring to FIG. 2, a dichroic film 8 is formed on one side of the optical crystal 6. The collimated infrared light 21b penetrates the dichroic film 8 and the collimated single band visible light 7 is reflected by the dichroic film 8. As shown in FIG. 1 and FIG. 2, in the optical crystal 6, the collimated infrared light 21b having the vibration spectrum and the collimated single band visible light 7 are coupled into sum-frequency light 24 when the requirements of phase-matching are satisfied. The requirements of phase-matching include two equations as follows:

$$1/\lambda_{ir}+1/\lambda_p=1/\lambda_s \quad (1),$$

$$n_o(\lambda_{ir})/\lambda_{ir}+n_o(\lambda_p)/\lambda_p=n_e(\lambda_s,\theta, T,V)/\lambda_s \quad (2)$$

wherein $\lambda_{ir}$ is the wavelength of the collimated infrared light 21b, $\lambda_p$ is the wavelength of the collimated single band visible light 7, $\lambda_s$ is the wavelength of the sum-frequency light 24, $n_o$ is ordinary ray refractive index, and $n_e$ is extraordinary ray refractive index.

In equation (1), the total energy of the collimated infrared light 21b and the collimated single band visible light 7 is equal to the energy of the sum-frequency light 24. In equation (2), the total momentum of the collimated infrared light 21b and the collimated single band visible light 7 is equal to the momentum of the sum-frequency light 24. Additionally, in equation (2), $n_e$ depends on the angle ($\theta$) of the optical crystal 6, the temperature (T) and voltage (V).

As shown in FIG. 1, the sum-frequency light 24 penetrates the dual color lens 13, the narrow band filter 19 and the ocular 9. The narrow band filter 19 further includes a notch filter 14 and a liquid crystal tunable filter 17. The narrow band filter 19 prevents passage of the collimated single band visible light 7. Then, the sum-frequency light 24 is received by the visible light image capturing device 10, such as a charge coupled device (CCD).

When the spectrum measuring apparatus measures the Raman and fluorescence spectra, the sample 20 is placed on the sample pedestal 4 and the laser source 11 outputs laser 22. The laser 22 becomes slightly divergent laser 16 after passing through the concave lens 12 and the convex lens 23. The slightly divergent laser 16 is reflected to the object lens 15 by the dual color lens 13. Then, regional illumination is generated on the sample 20 by the object lens 15. In this embodiment, the object lens 15 is an infinity-corrected object lens. After the sample 20 is stimulated by the laser 16, Raman light having various Raman spectra and fluorescence having various fluorescence spectra are generated thereof.

As shown in FIG. 1, the Raman light or fluorescence passes through the object lens 15, the dual color lens 13, the narrow band filter 19 and the ocular 9 in sequence. The narrow band filter 19 further includes the notch filter 14 and the liquid crystal tunable filter 17. The narrow band filter 19 prevents passage of the laser 16. Then, the Raman light or fluorescence is received by the visible light image capturing device 10, such as a CCD.

Figure 3A:
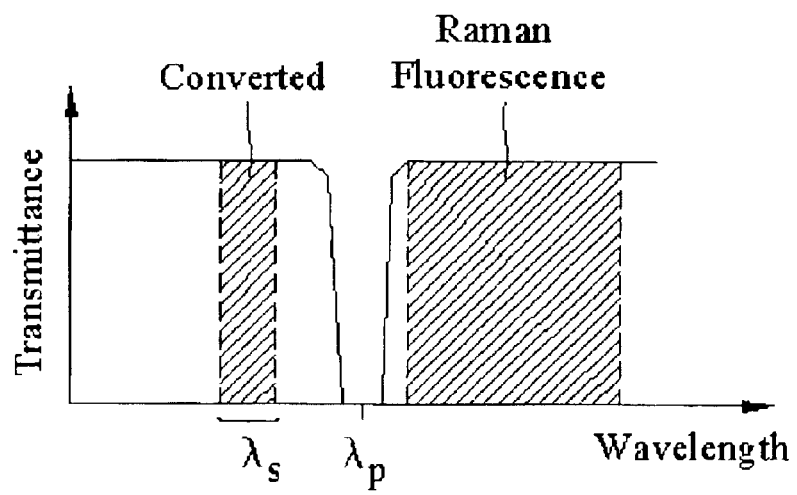
FIG. 3A is a schematic view showing the penetration spectrum of the notch filter.

Referring to FIG. 3A, the laser output from the laser source cannot pass through the notch filter 14.

Figure 3B:
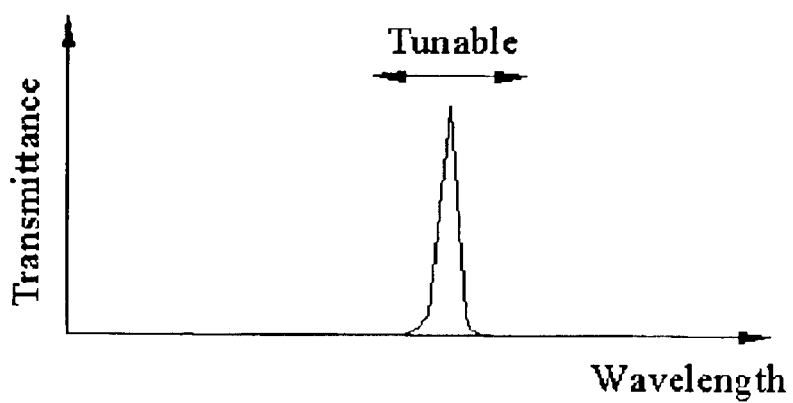
FIG. 3B is a schematic view showing the penetration spectrum of the liquid crystal tunable filter.

Referring to FIG. 3B, the liquid crystal tunable filter 17 allows the Raman light or fluorescence having particular wavelengths to pass. Furthermore, the Raman light or fluorescence having a predetermined wavelength is accentuated by the liquid crystal tunable filter 17.

While the invention has been described by way of examples and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A spectrum measuring apparatus for measuring infrared, Raman and fluorescence spectra, comprising:

a sample pedestal, wherein a sample is placed on the sample pedestal;

an infrared source, the infrared source outputting infrared light to the sample to generate infrared light having a vibration spectrum when the spectrum measuring apparatus measures the infrared spectrum;

a laser source, the laser source outputting single band laser to the sample when the spectrum measuring apparatus measures the Raman or fluorescence spectra;

an infrared up-conversion object lens having an optical crystal and an infrared object lens, wherein a dichroic film is formed on one side of the optical crystal, the infrared object lens receiving the infrared light having the vibration spectrum and outputting collimated infrared light having the vibration spectrum to the optical crystal when the single band laser enters the optical crystal and is reflected by the dichroic film, the single band laser and the collimated infrared light having the vibration spectrum coupled into sum-frequency light in the optical crystal;

an object lens, wherein the single band laser is output to the sample via the object lens when the spectrum measuring apparatus measures the Raman or fluorescence spectra, and the sample generates Raman light having the Raman spectrum or fluorescence having the fluorescence spectrum to pass through the object lens;

an ocular imaging the sum-frequency light, the Raman light and the fluorescence to a predetermined position; and a visible light image capturing device disposed on the predetermined position to receive the sum-frequency light, the Raman light and the fluorescence.

2. The spectrum measuring apparatus as claimed in claim 1, wherein the infrared object lens is an IR infinity-corrected reflective object lens.

3. The spectrum measuring apparatus as claimed in claim 1, wherein the optical crystal is a birefringence crystal.

4. The spectrum measuring apparatus as claimed in claim 1, wherein the optical crystal is a quasi-phase matching crystal.

5. The spectrum measuring apparatus as claimed in claim 1, further comprising a dual color lens, wherein the single band laser is reflected to the infrared up-conversion object lens or the object lens by the dual color lens, and the sum-frequency light, the Raman light and the fluorescence pass through the dual color lens.

6. The spectrum measuring apparatus as claimed in claim 1, further comprising a narrow band filter for preventing the single band laser from interfering with the visible light image capturing device.

7. The spectrum measuring apparatus as claimed in claim 6, wherein the narrow band filter further comprises a notch filter and a liquid crystal tunable filter.

8. The spectrum measuring apparatus as claimed in claim 1, wherein the visible light image capturing device is a charge coupled device (CCD).

9. The spectrum measuring apparatus as claimed in claim 1, wherein the object lens is an infinity-corrected object lens.

10. The spectrum measuring apparatus as claimed in claim 1, further comprising a concave lens and a convex lens, wherein the concave lens and the convex lens convert the laser output from the laser source into collimated laser when the spectrum measuring apparatus measures the infrared spectrum, and the concave lens and the convex lens convert the laser output from the laser source into slightly divergent laser when the spectrum measuring apparatus measures the Raman and fluorescence spectra.

11. The spectrum measuring apparatus as claimed in claim 1, further comprising an infrared condenser set reflecting the infrared light from the infrared source to the sample.

* * * * *